United States Patent [19]

Mielnik, Jr. et al.

[11] Patent Number: 4,526,165
[45] Date of Patent: Jul. 2, 1985

[54] APPARATUS FOR CONSTRAINING A HUMAN LIMB

[75] Inventors: Thaddeus J. Mielnik, Jr.; Robert A. Wolff, both of Erie, Pa.

[73] Assignee: American Sterilizer Company, Erie, Pa.

[21] Appl. No.: 546,277

[22] Filed: Oct. 28, 1983

[51] Int. Cl.³ .............................................. A61F 13/00
[52] U.S. Cl. ..................................... 128/133; 128/327
[58] Field of Search ................ 128/133, 134, 327; 269/328

[56] References Cited

U.S. PATENT DOCUMENTS

| | | | |
|---|---|---|---|
| 2,679,842 | 6/1954 | Brill | 128/134 |
| 2,991,785 | 7/1961 | Terrell | 128/134 |
| 3,027,895 | 4/1962 | Williams | 128/133 |
| 4,232,681 | 11/1980 | Tulaszewski | 128/133 |
| 4,299,213 | 11/1981 | Violet | 128/133 |

Primary Examiner—John D. Yasko
Attorney, Agent, or Firm—Robert D. Yeager; Andrew J. Cornelius

[57] ABSTRACT

A limb restraint permits proper positioning of a limb of a patient while medical or surgical operations are being performed on the patient. The preferred embodiment includes a fixed restraint and an adjustable restraint which cooperate with each other to encircle the limb and hold it in place. One end of the adjustable restraint can be wound around or unwound from a spool using a handle assembly to tighten or loosen, respectively, the restraint on the limb. A clutch is provided to prevent the spool from rotating in a direction that would loosen the restraint. The handle assembly used to tighten or loosen the restraint prevents inadvertent tightening or loosening of the restraint when the handle assembly is not in use.

7 Claims, 7 Drawing Figures

APPARATUS FOR CONSTRAINING A HUMAN LIMB

BACKGROUND OF THE INVENTION

1. Field of the Invention

The present invention relates generally to apparatus used during performance of surgical procedures and, more particularly, to apparatus for securing a limb of a patient while medical or surgical procedures are performed on the patient.

2. Description of the Prior Art

Often it is necessary to secure a limb of a patient in a desired position during the performance of many medical and surgical procedures. For example, current trends in orthopedic surgery show increasing use of "keyhole" type surgical procedures for performing joint surgery. It is common during the performance of keyhole, including arthroscopic, surgical procedures to insert viewing and cutting instruments into the joint through small puncture wounds formed in the skin. Often, it is necessary to fix the position of the limb to facilitate manipulation of the joint to properly position the viewer or the cutter within the joint.

Conventional limb restraints employ a type of clamp which bears some resemblance to an ordinary clamp. The clamp exerts pressure on the limb at, essentially, two points on opposing sides of the limb. Because the restraint contacts the limb at only two locations, the force exerted by the restraint at those locations must be relatively high to permit proper positioning of the limb. Accordingly, pinching, sore spots and sensory loss can be experienced by a limb when constrained by a conventional limb restraint. Further, the degree to which a limb can be constrained by a conventional restraint is not as great as can be attained through use of a restraint that makes contact with the limb at more than two points. U.S. Pat. Nos. 4,181,297 and 4,252,306 show clamp restraints.

Performing arthroscopic surgery using the supra patellar approach involves insertion of a viewing instrument and a cutting instrument through a puncture wound formed just to the thigh side of the kneecap. During performance of arthroscopic knee surgery using the supra patellar approach, a limb restraint should be used to fix the position of the thigh. Many conventional limb restraints are so thick or bulky that they impede the manipulations of the viewer and cutter that must be achieved to employ the supra patellar approach.

U.S. Pat. No. 4,299,213, issued to James T. Violet, shows a leg stabilizer (the "Violet stabilizer") which employs an inflatable restraint. Use of the Violet stabilizer presents several problems. Several of the problems are due to the use of an inflatable restraint, which presents the risk that either a puncture of the restraint or a failure of the source of air pressure will render the Violet stabilizer virtually useless. Further, the forces applied to the lower leg as the surgeon flexes the lower leg during the performance of arthroscopic knee surgery will cause the restrained portion of the leg to shift within the inflatable restraint.

Accordingly, there exists a need for a limb restraint that provides a higher degree of limb fixation than that achieved by a conventional restraint that clamps the limb at two points, and that causes less physiological damage to the limb than that caused by the conventional restraints. Further, there exists a need for a limb restraint that does not impede employment of the supra patellar approach to arthroscopic knee surgery.

SUMMARY OF THE INVENTION

The present invention provides apparatus for restraining movement of a portion of a human limb. The invention includes a restraint adapted to encircle the limb including a member that is adapted to contact a limb along its entire circumference and that is constructed, at least in part, from a shock absorbing material. The invention includes a support that is adapted for mounting to a surgical table. The support has apparatus for selectively tightening the restraint around the limb to cause the restraint to exert force against the limb that is substantially uniform along its circumference. The tightening apparatus tightens the restraint around the limb by reducing the length of the portion of the restraint that bears against the limb.

Preferably, the restraint is a restraining member that defines at least one padded restraint. The tightening apparatus can include a spool mounted to the support for rotational movement relative to the support. The restraining member can define a fixed padded restraint secured to the support and an adjustable padded restraint, one end of which is secured to the spool. Rotation of the spool causes the adjustable padded restraint to wrap around or become unwrapped from the spool, to tighten or loosen, respectively, the adjustable padded restraint around the limb. An operator can be operably connected to the spool for causing rotation of the spool in one direction only when the operator is rotated. The invention can include apparatus for allowing rotation of the spool in only one direction.

Preferably, the invention includes a clutch which transfers force from the operator to the spool only when the magnitude of the resistance to rotation offered by the spool is less than a predetermined value. Accordingly, the clutch can be set to prevent overtightening of the restraint against the limb.

The apparatus can include an operator that is so connected to the spool that it can assume an inoperative position in which rotation of the operator does not cause rotation of the spool. The apparatus can further include apparatus, such as a spring, for urging the operator towards its inoperative position. Thus, inadvertent tightening of the restraint around the limb is prevented.

The padded restraint can be a belt constructed of steel mesh to which a shock absorbing member is attached for contact with a limb. One end of the belt is secured to the spool. The belt absorbs the force exerted by rotation of the spool on the restraint and, thus, prevents the shock absorbing member from becoming stretched.

The limb restraint of the present invention contacts substantially all points on the circumference of a section of the limb. Accordingly, the limb restraint distributes the applied force substantially uniformly around the circumference of the limb and fixes the position of the limb to a greater extent than conventional limb restraints. Further, the distribution of force provided by the present invention yields a restraint that can apply the same total force to a limb as that applied by a conventional clamp restraint, but that applies its force over a larger area of the limb. Therefore, the conventional clamp restraint is more likely than the invention to cause physiological damage to the limb, especially when a surgeon is manipulating the limb as a surgical procedure is being performed.

Moreover, the present invention permits employment of a restraint which does not impede use of the supra patellar approach to arthroscopic knee surgery.

BRIEF DESCRIPTION OF THE DRAWINGS

The following detailed description of the preferred embodiments can be understood better if reference is made to the drawings, in which.

DETAILED DESCRIPTION OF THE PREFERRED EMBODIMENTS

Figure 1:
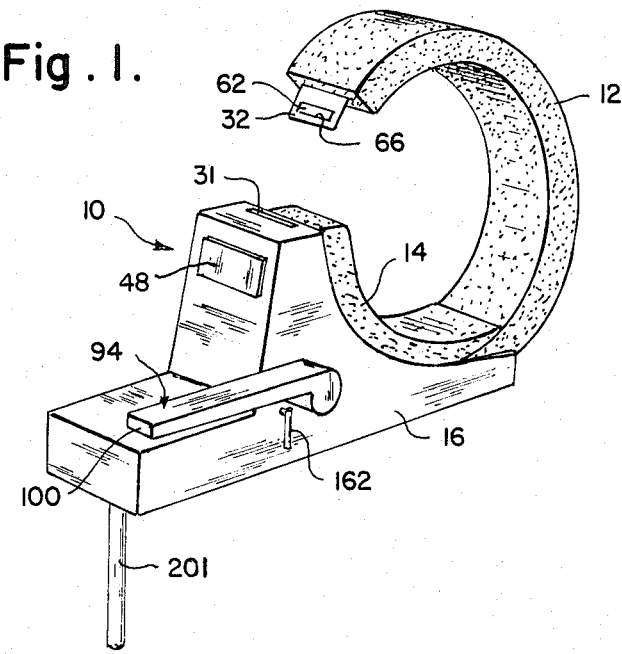
FIG. 1 is an isometric view of a limb restraint that is the preferred embodiment of the present invention.
Figure 2:
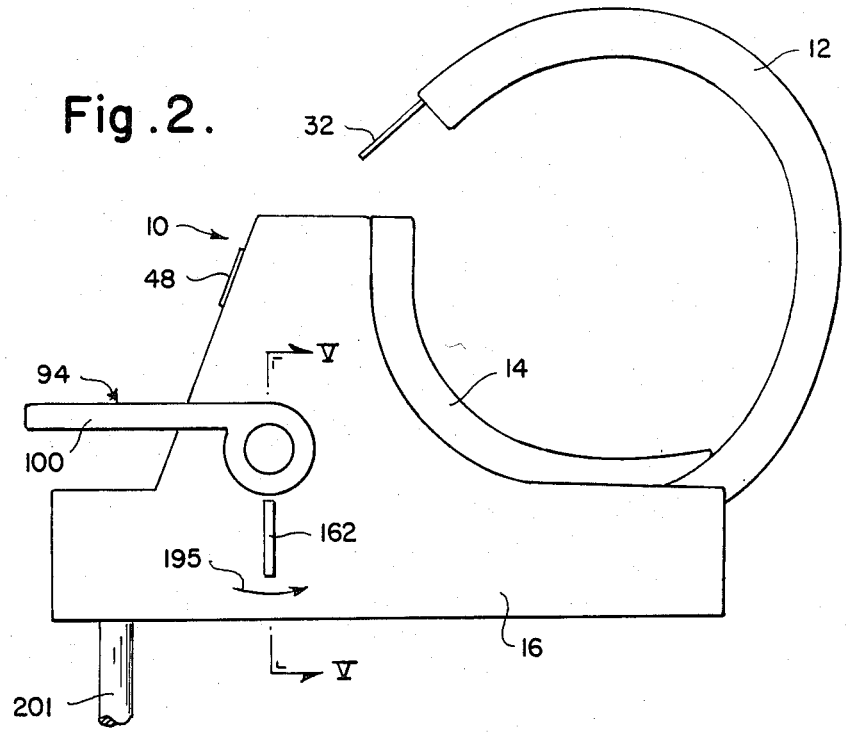
FIG. 2 is a side elevational view of the limb restraint shown in FIG. 1.
Figure 3:
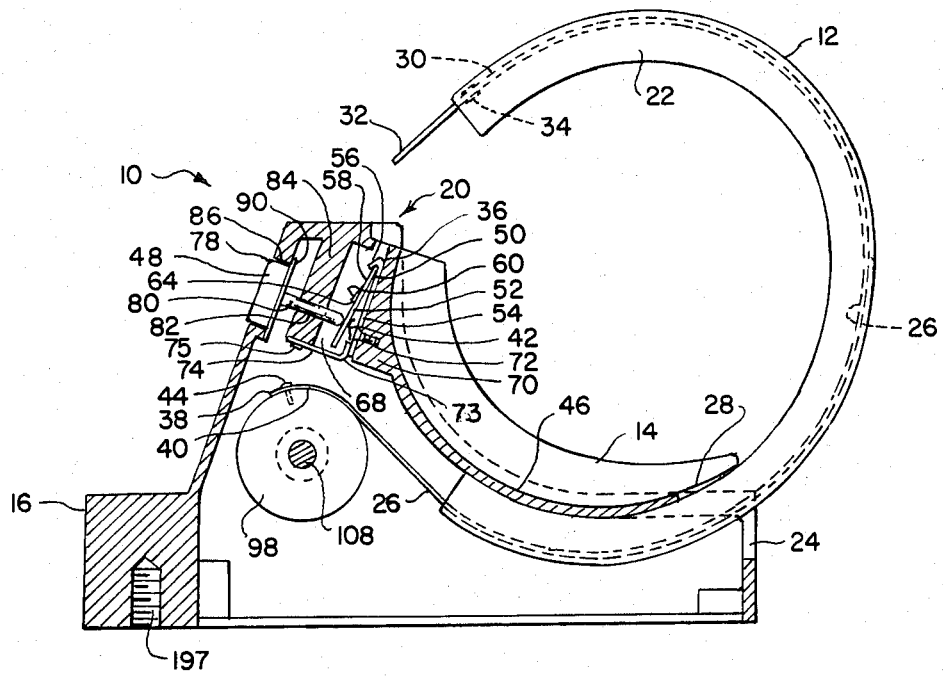
FIG. 3 is a side elevational view, partially in section, of the limb restraint shown in FIG. 1.
Figure 7:
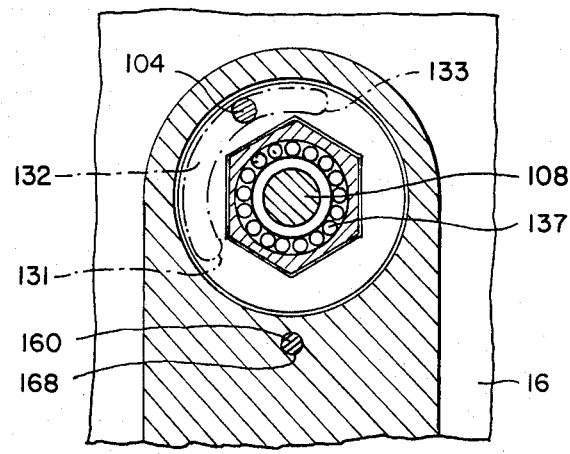
FIG. 7 is a sectional view of a portion of the limb restraint shown in FIG. 4 taken along the line VII—VII.
Figure 4:
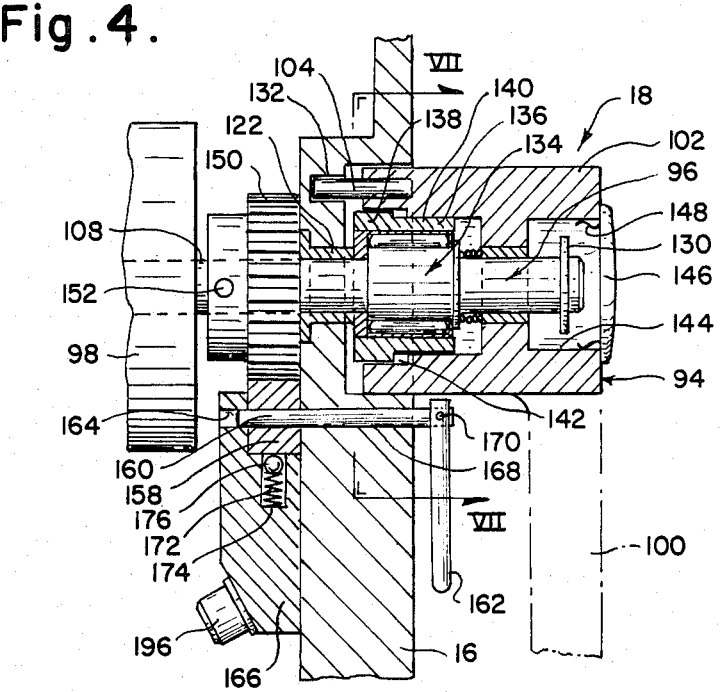
FIG. 4 is a front view, partially in section, of a portion of the limb restraint shown in FIG. 1, with the handle in the drive position.

FIGS. 1 through 7 show limb restraint 10, which is the preferred embodiment of the present invention. Generally, limb restraint 10 includes adjustable restraint 12, fixed restraint 14, housing 16 cast of aluminum, tightening mechanism 18 and restraint fastener 20.

Adjustable restraint 12 includes a pad 22, constructed of self-skinned urethane foam, which encloses a flexible steel mesh belt 26. Steel belt 26 absorbs the force experienced by adjustable restraint 12 during use of leg restraint 10 and prevents pad 22 from becoming stretched or otherwise deformed. One end 30 of steel belt 26 is secured to a belt latch 32 with a suitable fastener 34. Belt latch 32 defines an opening 62 which is adapted to engage restraint fastener 20. As is described more fully below, latch 32 is inserted into housing 16 through opening 31 to engage restraint fastener 20. The remaining end 40 of steel belt 26 is secured by any suitable means to a steel strip 38. Steel strip 38 is secured to the outer surface of a spool 98 (which is described in greater detail below) with a pair of suitable fasteners 44 (only one shown) each of which passes through an opening (not shown) in strip 38. Housing 16 defines an opening 24 through which end 40 of belt 26 can be passed to secure steel strip 38 to spool 98. Belt 26 is adapted to be wound around or unwound from spool 98 as spool 98 is rotated.

Fixed restraint 14 is formed from flexible foam and is secured to surface 46 of housing 16. Fixed restraint 14 overlaps adjustable restraint 12 at area 28 to ensure that, when latch 32 is engaged with restraint fastener 20, fixed restraint 14 and adjustable restraint 12 can cooperate to completely encircle and restrain a limb and exert a force of substantially uniform magnitude along the circumference of the limb.

Restraint fastener 20 includes release button 48 and spring loaded lock 50. Lock 50 includes a locking plate 52 and a mounting plate 54. One end of mounting plate 54 defines a lip 36 which receives the lip of a spring steel clip 42. End 56 of locking plate 52 is disposed within the lip of clip 42. Clip 42 urges locking plate 52 away from mounting plate 54. The lip of clip 42 and lip 36 of mounting plate 54 hold end 56 of locking plate 52 within lip 36. Accordingly, clip 42 tries to pivot locking plate 52 about its end 56. Surface 58 of locking plate 52 defines a protrusion 60 which is adapted to be received by latch opening 62. Protrusion 60 includes a surface 64 which is adapted to engage edge 66 of opening 62 to prevent latch 32 from being withdrawn from housing 16. Lock 50 is secured within chamber 68, which is formed by housing 16, to mounting 70, which also is formed by housing 16, with any suitable fastener 72. A bottom plate 74 is secured to mounting 84 with a suitable fastener 75. Bottom plate 74 defines a flange 73 which bears against an end of mounting plate 54 and against the clip portion of clip 42 to hold clip 42 in place.

Release button 48 includes a depressor 78 and an actuator 80. Actuator 80 extends from depressor 78 through passage 82 formed in mounting 84 and engages locking plate 52 to limit the extent to which clip 42 can pivot locking plate 52 around its end 36. Depressor 78 is disposed generally within opening 86 formed by housing 16. A back clip 90 is secured to actuator 80 between mounting 84 and front wall 92 of housing 16. Back clip 90 bears against the inner surface of front wall 92 to prevent clip 42 from ejecting release button 48 from housing 16.

Tightening mechanism 18 includes a handle assembly 94 which is adapted to drive a shaft assembly 96. Generally, rotation of handle assembly 94 causes rotation of spool 98 through shaft assembly 96. Rotation of spool 98 changes the portion of adjustable restraint 12 that is not enclosed by housing 16 and that is available for wrapping around the limb of a patient. Therefore, rotation of spool 98 adjusts the force exerted by restraints 12 and 14 on a limb constrained by restraint 10. Shaft assembly 96 includes apparatus for enabling shaft assembly 96 to transmit rotational motion from handle assembly 94 to spool 98 when handle 94 is rotated in one direction and for preventing shaft assembly 96 from transmitting rotational motion to spool 98 when handle assembly 94 is rotated in the remaining direction. Further, shaft assembly 96 includes mechanism which can be used to prevent spool 98 from being rotated inadvertently to decrease the tension on adjustable restraint 12 when adjustable restraint 12 is under tension.

Handle assembly 94 includes grip 100 and shaft housing 102. A stop 104 protrudes from end 106 of housing 102. Shaft assembly 96 includes a shaft 108 and a bearing 112 which is disposed within opening 114 formed by housing 102 and receives and supports end 110 of shaft 108. A bearing 116 is disposed within opening 118 formed by housing 16 and receives and supports end 120 of shaft 108. Shaft 108 is further supported intermediate its ends by a bearing 122 which is disposed within opening 124 formed by housing 16.

Figure 5:
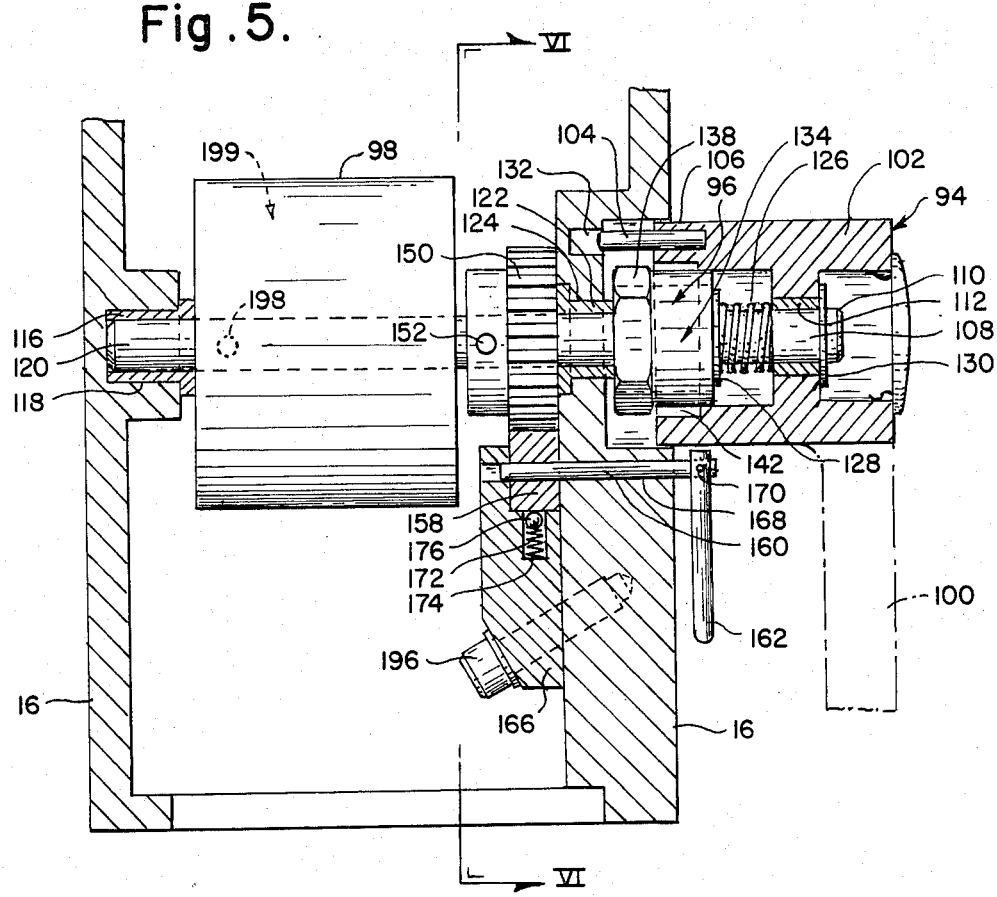
FIG. 5 is a side sectional view of a portion of the limb restraint shown in FIG. 2 taken along the line V—V, with the handle in the disengaged position.

A spring 126 is mounted on shaft 108 between a snap ring 128 and bearing 112. Spring 126 urges handle assembly 94 toward its disengaged position, which is shown in FIG. 5, to prevent inadvertent tightening of restraint 10 by unintended contact with grip 100. Outward travel of handle assembly 94 is limited by snap ring 130 which is mounted to end 110 of shaft 108. Regardless of the axial position of handle assembly 94, a portion of stop 104 is disposed within slot 132, which is formed by housing 16. As can be seen best in FIGS. 6 and 7, slot 132 coincides with a portion of the path of rotation that stop 104 follows around shaft 108 as handle assembly 94 is rotated. Accordingly, ends 131 and 133 of slot 132 function as limits to the travel of stop 104 and limit the rotation of handle assembly 94 to the arc defined by slot 132. Preferably, slot 132 encompasses 135°. Handle assembly 94 can be slid along shaft 108 between its drive position, shown in FIG. 4 and in which stop 104 preferably contacts the base of slot 132, and its disengaged position, in which bearing 112 contacts snap ring 130, and can be rotated through the arc encompassed by slot 132. Handle assembly 94 is in its beginning position when stop 104 is in contact with limit 131 and is in its ending position when stop 104 is in contact with limit 133.

A conventional multiple disc friction clutch 199 is disposed on shaft 108 within spool 98. Clutch 199 transmits rotational motion from shaft 108 to spool 98 only when spool 98 offers resistance to rotation of shaft 108 that is less than a predetermined magnitude. A drawn cup clutch 134 is disposed on shaft 108 between snap ring 128 and bearing 122. As can be seen best in FIG. 4, clutch 134 includes a clutch housing 136 which defines a portion 138 having a hexagonal cross-sectional shape, and a portion 140 which has a cylindrical cross-sectional shape. Housing 102 of handle assembly 94 defines an opening 142 which is hexagonal in cross-sectional shape. Hexagonal portion 138 and hexagonal opening 142 are so sized that opening 142 receives hexagonal portion 138 when handle assembly 94 is in the drive position. When handle assembly 94 is in the drive position, the surface defining opening 142 contacts hexagonal portion 138 and rotation of handle assembly 94 causes corresponding rotation of clutch housing 136. Clutch 134 can be any suitable clutch such as a clutch that transmits rotation between the clutch housing and the shaft disposed within the clutch member of the clutch when either the shaft or the housing is rotated in one direction and prevents transmission of rotation between the housing and the shaft when the housing or the shaft is rotated in the remaining direction. A suitable clutch is manufactured by the Torrington Company and is referred to commonly as a Torrington Clutch. Clutch 199 provides primary protection from overtightening of restraint 10 that could cause thromboembolism or neurovascular compression. Clutch 134 is set to slip at a resistance that is slightly higher than that at which clutch 199 is set and provides backup protection from overtightening in case clutch 199 fails.

Housing 102 also defines an access opening 144 which permits placement of snap ring 130 on shaft 108 when handle assembly 94 is being assembled. A circular cover 146 includes flexible steel members 148 which can be inserted within opening 144 to secure cover 146 over opening 144 and protect shaft 108 from foreign matter.

Restraint 10 also includes a ratchet and pawl assembly which prevents adjustable restraint 12 from slipping. Ratchet 150 is mounted to shaft 108 with a set screw 152 between spool 98 and bearing 122. Ratchet 150 includes a portion defining teeth 156 which are adapted to engage a pawl 158. Pawl 158 is mounted on and rotates with a pawl shaft 160. Pawl shaft 160 is disposed and supported at one end within a bore 164 defined by a mounting block 166. The remaining end of pawl shaft 160 is disposed and supported within a bore 168 defined by housing 16. Lever 162 is fixed to shaft 160 with a pin 170 and can be rotated to cause rotation of shaft 160. A spring 172 is disposed within a seat 174 and urges a ball 176 toward pawl 158.

Pawl 158 defines notches 178 and 180, which are adapted to engage teeth 156 of ratchet 150. Pawl 158 also defines seats 182 and 184 which are adapted to receive ball 176.

Figure 6:
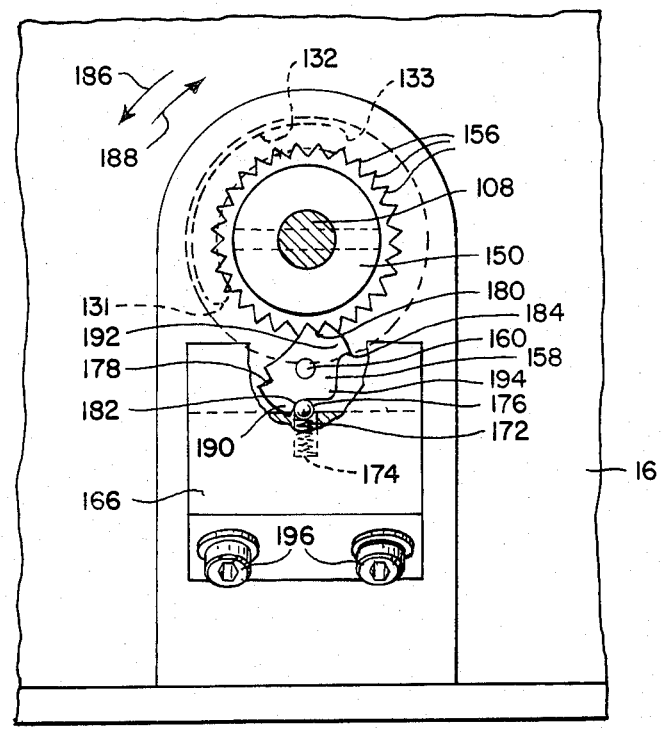
FIG. 6 is a view, partially cut away, of a portion of the limb restraint shown in FIG. 5, taken along the line VI—VI.

When ball 176 is seated on seat 182, ratchet 150 can be rotated in the direction indicated by arrow 186 in FIG. 6. Rotation of ratchet 150 in the direction indicated by arrow 188 is prevented by cooperation between ball 176, seat 174 and stop 190 of pawl 158. Similarly, ratchet 150 can be rotated in the direction indicated by arrow 188 in FIG. 6 when ball 176 is seated on seat 184. Rotation of ratchet 150 in the direction indicated by arrow 186 is prevented by cooperation between ball 176, seat 174 and stop 192 of pawl 158. Rotation of lever 162 causes rotation of pawl 158 and permits spring 172 to seat ball 176 on seat 182 or 184, as desired. Protrusion 194 of pawl 158 ensures that ball 176 always will be seated on either seat 182 or 184.

Mounting block 166, which receives one end of pawl shaft 160, spring 172 and ball 176, is secured to the inside of housing 16 with a pair of suitable bolts 196 (only one shown). Spool 98 is mounted on shaft 108 between bearing 116 and ratchet 150 with two suitable fasteners 198 disposed 90° from each other (only one shown). A steel strip 38 is secured by any suitable means to end 40 of steel belt 26. Steel belt 26 is secured to spool 98 at end 40 with two fasteners 44 (only one shown) which pass through openings defined by steel strip 38.

Limb restraint 10 can be secured in any acceptable fashion to a suitable support. Typically, a support rod 201 is threaded within threaded opening 197 formed by housing 16. A conventional clamp can be used to clamp support 201 to such a support as a surgical table. The limb of the patient is placed on fixed restraint 14. Lever 162 is rotated in the direction opposite to that indicated by arrow 195 in FIG. 2 until ball 176 is seated on seat 182. Then, flexible belt 26 is unwound from spool 98 and latch 32 is inserted into opening 68 until protrusion 60 passes through latch opening 62.

Lever 162 is rotated in the direction indicated by arrow 195 until ball 176 is seated on seat 184. Handle assembly 94 is moved toward housing 16 until handle assembly 94 reaches its drive position. While maintaining sufficient pressure on handle assembly 94 to keep it in its drive position, handle assembly 94 is rotated from its beginning position toward its ending position, which causes clutch housing 136, clutch member 137 and shaft 108 to rotate in the same direction. Rotation of shaft 108 in the direction indicated by arrow 195 causes clutch 199 to rotate spool 98 in the same direction, to wrap steel belt 26 around spool 98 and to tighten the restraint 10 around the limb.

If the proper degree of tightness is achieved before handle assembly 94 reaches its ending position, handle assembly 94 is released and spring 126 urges handle assembly 94 away from housing 16 into its disengaged position to prevent inadvertent tightening of restraint 10 around the limb. If the proper degree of tightness is not achieved before hahdle assembly 94 reaches its ending position, handle assembly 94 is rotated toward its beginning position. Rotation of handle assembly 94 toward its beginning position does not cause rotation of shaft 108 because housing 136 and clutch member 137 slide over shaft 108 without rotating it. Accordingly, handle assembly 94 need not be moved to its disengaged position each time it is rotated toward its beginning position from its ending position. When ball 176 is seated on seat 184, stop 192, ball 176 and seat 174 prevent ratchet 150, shaft 108 and spool 98 from rotating in the direction indicated by arrow 186 in FIG. 6, thus preventing a decrease in tightness when restraints 12 and 14 are restraining a limb.

To remove a limb from restraint 10, depressor 78 of release button 48 is pushed toward housing 16 to cause actuator 80 to move locking plate 52 toward mounting plate 54 until protrusion 60 is no longer disposed within latch opening 62. Latch 32 is withdrawn from housing 16 and the limb is removed from restraint 10.

What is claimed is:

1. Apparatus for restraining movement of a portion of a human limb comprising:

a restraint adapted to encircle the limb including a member that is adapted to contact the limb along its entire circumference and that is constructed from a shock absorbing material, said restraint being a restraining member defining at least one padded restraint; and a support adapted for mounting to a surgical table, said support having means for selectively tightening said restraint around the limb to cause said restraint to exert force against the limb that is substantially uniform along its circumference;

said tightening means tightening said restraint around the limb by reducing the length of the portion of said restraint that bears against the limb, said tightening means including a spool mounted to said support for rotational movement relative to said support, one end of said padded restraint being secured to said spool, rotation of said spool causing said padded restraint to wrap around or unwrap from said spool to tighten or loosen, respectively, said padded restraint around the limb, and an operator operably connected to said spool for causing rotation of said spool when said operator is rotated in one direction only.

2. The apparatus recited in claim 1 wherein said restraining member defines a fixed padded restraint secured to said support and an adjustable padded restraint, one end of said adjustable padded restraint being secured to said spool, said fixed and adjustable padded restraints cooperating to encircle the limb.

3. The apparatus recited in claim 1 further comprising means for allowing rotation of said spool in only one direction.

4. The apparatus recited in claim 1 further comprising a clutch which transfers force from said operator to said spool only when the magnitude of the resistance to rotation offered by said spool is less than a predetermined value.

5. The apparatus recited in claim 1 wherein said operator is so connected to said spool that it can assume an inoperative position in which rotation of said operator does not cause rotation of said spool and wherein said apparatus further comprises means for urging said operator toward its inoperative position.

6. The apparatus recited in claim 1 wherein said padded restraint is a belt constructed of steel mesh to which a shock absorbing member is attached for contact with the limb, one end of said belt being secured to said spool.

7. Apparatus for restraining movement of a portion of a human limb comprising:

a restraint adapted to encircle the limb, said restraint including a belt constructed of steel mesh to which a shock absorbing member is attached for contact with the limb;

a support adapted for mounting to a surgical table, said tightening means including a spool mounted to said support for rotational movement relative thereto, one end of said belt being secured to said spool;

an operator mounted for movement relative to said support;

a clutch operably connected between said operator and said spool, said clutch transferring force from said operator to rotate said spool only when the magnitude of the resistance to rotation of said spool is less than a predetermined value;

means for allowing rotation of said spool in one direction only; and means for biasing said operator toward a position in which movement of said operator does not cause rotation of said spool.

* * * * *